(12) United States Patent  (10) Patent No.: US 8,524,915 B2
Schleth et al.                (45) Date of Patent:    *Sep. 3, 2013

(54) PROCESS FOR THE PREPARATION OF PYRAZOLE CARBOXYLIC ACID AMIDES

(75) Inventors: Florian Schleth, Munchwilen (CH); Thomas Vettiger, Munchwilen (CH); Michael Rommel, Munchwilen (CH); Hans Tobler, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/642,511

(22) PCT Filed: Apr. 14, 2011

(86) PCT No.: PCT/EP2011/055870
§ 371 (c)(1),
(2), (4) Date: Oct. 19, 2012

(87) PCT Pub. No.: WO2011/131544
PCT Pub. Date: Oct. 27, 2011

(65) Prior Publication Data
US 2013/0041160 A1    Feb. 14, 2013

(30) Foreign Application Priority Data

Apr. 20, 2010 (EP) .................... 10160439

(51) Int. Cl.
C07D 231/10 (2006.01)
C07C 25/18 (2006.01)

(52) U.S. Cl.
USPC ...................... 548/374.1; 570/183

(58) Field of Classification Search
USPC ..................... 548/374.1; 570/183
See application file for complete search history.

(56) References Cited

FOREIGN PATENT DOCUMENTS

| WO | 2007/048556 | 5/2007 |
|----|-------------|--------|
| WO | 2007/068417 | 6/2007 |
| WO | 2009/138375 | 11/2009 |
| WO | 2010/072631 | 7/2010 |

OTHER PUBLICATIONS

International Search Report, International Application No. PCT/EP2011/055870, completion date: May 23, 2011.

*Primary Examiner* — Joseph K. McKane
*Assistant Examiner* — Samantha Shterengarts
(74) *Attorney, Agent, or Firm* — R. Kody Jones

(57) ABSTRACT

The invention relates to a process for the preparation of a compound of formula (I), which process comprises a) reacting a compound of formula (II), wherein X is chloro or bromo, with an organometallic species to (III) reacting the halobenzyne of formula (III) so formed with (IV) wherein $R^1$ and $R^2$ are hydrogen or $C_1$-$C_6$alkyl; to (V), b) hydrogenating V in the presence of a metal catalyst to (VI), c) ozonising (VI) to (VII) d) converting (VII) in the presence of a phosphane and $CCl_4$ or $CHCl_3$ to (VIII) (VIII), and either e1) reacting VIII with $NH_3$ in the presence of a catalyst to (IX) and f) reacting IX in the presence of a base with the compound of formula (X), to the compound of formula (I); or e2) reacting the compound of formula (VIII), in the presence of a solvent, a base, a copper catalyst and at least one ligand with (Xa), to the compound of formula (I).

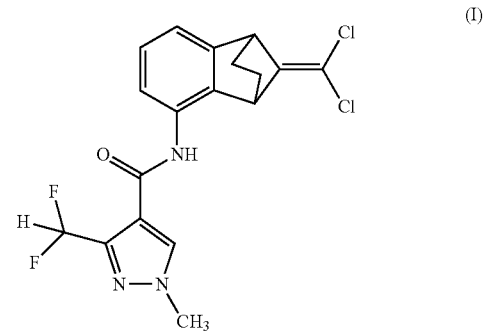

(I)

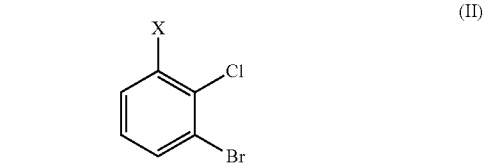

(II)

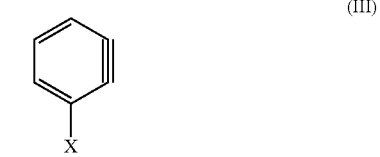

(III)

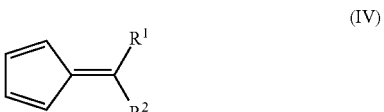

(IV)

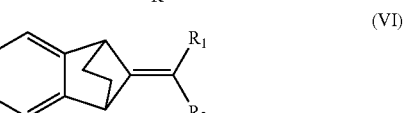

(VI)

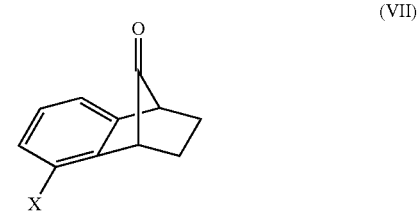

(VII)

-continued
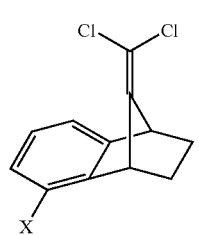 (VIII)
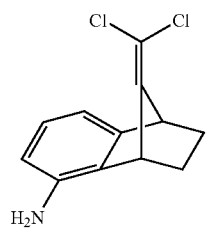 (IX)
-continued
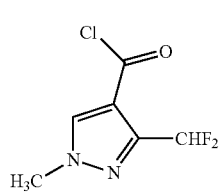 (X)
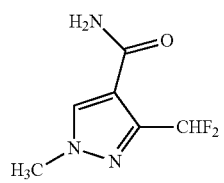 (Xa)
6 Claims, No Drawings

PROCESS FOR THE PREPARATION OF PYRAZOLE CARBOXYLIC ACID AMIDES

This application is a 371 of International Application No. PCT/EP2011/055870 filed Apr. 14, 2011, which claims priority to EP 10160439.5 filed Apr. 20, 2010, the contents of which are incorporated herein by reference.

The present invention relates to a process for the preparation of 3-difluoromethyl-1-methyl-1H-pyrazole-4-carboxylic acid (9-dichloromethylene-1,2,3,4-tetrahydro-1,4-methano-naphthalen-5-yl)-amide and to novel intermediates useful for this process.

The compound 3-difluoromethyl-1-methyl-1H-pyrazole-4-carboxylic acid (9-dichloromethylene-1,2,3,4-tetrahydro-1,4-methano-naphthalen-5-yl)-amide and its microbicidal properties is described for example in WO 2007/048556.

The preparation of 3-difluoromethyl-1-methyl-1H-pyrazole-4-carboxylic acid (9-dichloromethylene-1,2,3,4-tetrahydro-1,4-methano-naphthalen-5-yl)-amide is known from WO 2007/048556. Said compound can be prepared according to schemes 1 and 4 by a) reacting the compound of formula A

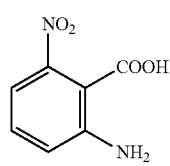

(A)

in the presence of an alkyl nitrite with a compound of formula B

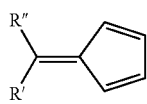

(B)

wherein R' and R" are e.g. $C_1$-$C_4$alkyl, to a compound of formula C

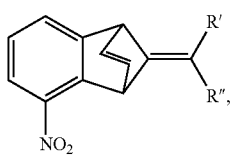

(C)

b) hydrogenating the compound of formula C in the presence of a suitable metal catalyst to a compound of formula D

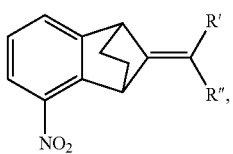

(D)

c) ozonising the compound of formula D and subsequent treatment with a reducing agent to a compound of formula E

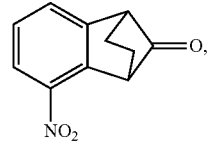

(E)

d) reacting the compound of formula E in the presence of triphenylphosphane/carbon tetrachloride to 2,9-dichloromethylidene-5-nitro-benzonorbornene of formula F

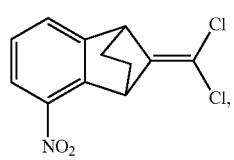

(F)

e) hydrogenating the compound of formula F in the presence of a metal catalyst to 2,9-dichloromethylidene-5-amino-benzonorbornene of formula G

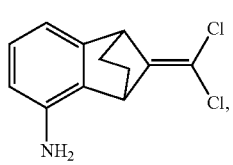

(G)

f) and reacting the compound of formula G with a compound of formula H

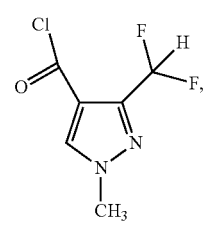

(H)

to 3-difluoromethyl-1-methyl-1H-pyrazole-4-carboxylic acid (9-dichloromethylene-1,2,3,4-tetrahydro-1,4-methano-naphthalen-5-yl)-amide.

A significant disadvantage of this prior art process is the high production costs which makes this process uneconomical and especially unsuitable for a large-scale production.

The aim of the present invention is therefore to provide a novel process for the production of 3-difluoromethyl-1-methyl-1H-pyrazole-4-carboxylic acid (9-dichloromethylene-1,2,3,4-tetrahydro-1,4-methano-naphthalen-5-yl)-amide that avoids the disadvantage of the known process and makes it possible to prepare 3-difluoromethyl-1-methyl-1H-pyrazole-4-carboxylic acid (9-dichloromethylene-1,2,3,4-tetrahydro-1,4-methano-naphthalen-5-yl)-amide in high yields and good quality in an economically advantageous way.

Thus, according to the present invention, there is provided a process for the preparation of the compound of formula I

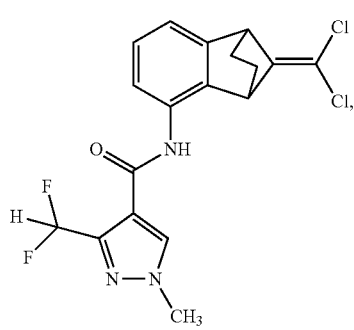 (I)

which process comprises
a) reacting a compound of formula II

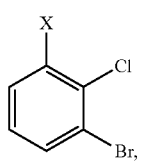 (II)

wherein X is chloro or bromo, with an organometallic species such as a $C_{1-6}$ alkyl- or phenyllithium or a $C_{1-6}$ alkyl- or a phenylmagnesium halide in an inert atmosphere to a halobenzyne of formula III

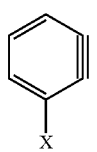 (III)

wherein X is chloro or bromo; reacting the halobenzyne of formula III so formed with a fulvene of formula IV

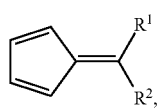 (IV)

wherein $R^1$ and $R^2$ are independently hydrogen or $C_1$-$C_6$alkyl; to a compound of formula V

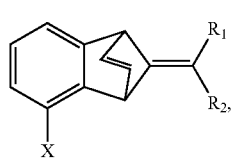 (V)

wherein $R^1$ and $R^2$ are independently hydrogen or $C_1$-$C_6$alkyl and X is chloro or bromo;

b) hydrogenating the compound of formula V in the presence of a suitable metal catalyst to a compound of formula VI

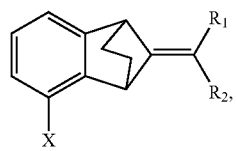 (VI)

wherein $R^1$ and $R^2$ are independently hydrogen or $C_1$-$C_6$alkyl and X is chloro or bromo;

c) ozonising the compound of formula VI to a compound of formula VII

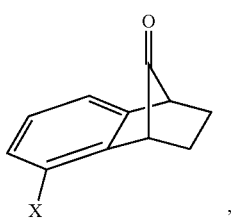 (VII)

wherein X is chloro or bromo;

d) converting the compound of formula VII in the presence of a phosphane and $CCl_4$ or $CHCl_3$ to the compound of formula VIII

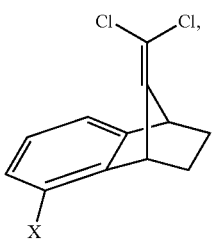 (VIII)

wherein X is chloro or bromo; and either e1) reacting the compound of formula VIII with $NH_3$ in the presence of a catalyst comprising palladium and at least one ligand to the compound of formula IX

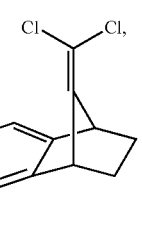 (IX)

and f) reacting the compound of formula IX in the presence of a base with the compound of formula X

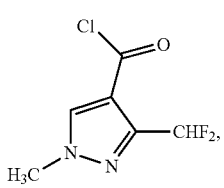

to the compound of formula I; or e2) reacting the compound of formula VIII

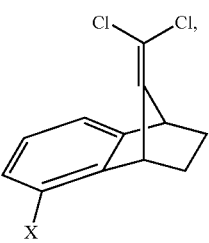

wherein X is chloro or bromo, preferably bromo; in the presence of a solvent, a base, a copper catalyst and at least one ligand with the compound of formula Xa

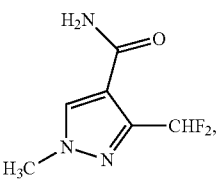

to the compound of formula I.

A further significant advantage of this invention over prior art processes is that the use of unstable dichlorofulvene is not necessary.

$R^1$ and $R^2$ are both preferably methyl.

Reaction step a):

The compound of formula II, wherein X is bromo, is known and disclosed, for example, in Recueil des Travaux Chimiques des Pays-Bas, 81, 365 (1962). The compound of formula II, wherein X is chloro or bromo, is disclosed, for example in WO 2008/049507. 1-bromo-2,3-dichloro-benzene may be prepared by the so-called Sandmeyer reaction from 2,3-dichloro-aniline. Such Sandmeyer reactions can be performed either by using an organic nitrite ester, such as tert-butyl nitrite or iso-pentyl nitrite, in an organic solvent, such as acetonitrile, in the presence of cupric bromide as brominating agent (as described in Journal of Organic Chemistry, 1977, 42, 2426-31) or by a two-step reaction involving diazotation in an acidic aqueous reaction media at temperatures of 0° C. to 15° C. using inorganic nitrite and then adding the reaction mixture to cuprous bromide solution (as described in Recueil des Travaux Chimiques des Pays-Bas et de la Belgique, 1932, 51, 98-113 and JP-6-2114-921).

The compounds of formula IV are known and described, for example in WO 2007/068417. Depending on how the halobenzyne of formula III is generated, the process is carried out in an organic solvent such as tetrahydrofuran, 1,4-dioxane, dimethoxyethane, diethyl ether, tert-butyl methyl ether, methyl-ethyl-ketone, ethyl acetate, methylacetate or an aromatic or aliphatic hydrocarbon, for example, toluene, xylene, benzene, hexane, pentane or a petroleum ether, and at a temperature of from −20° C. to +10° C., which may be elevated to ambient temperature or to a higher temperature to complete the reaction.

Preferred organometallic species for this reaction step are $C_{1-6}$ alkyl- or phenyllithium or $C_{1-6}$ alkyl- or phenylmagnesium halides, in particular n-butyllithium, isopropylmagnesium bromide or isopropylmagnesium chloride.

The 5-chloro- or 5-bromobenzonorbornadiene of the formula (V) may be isolated by quenching the reaction mixture in an aqueous medium, for example, in saturated ammonium chloride solution, extracting the product in a solvent such as ethyl acetate, washing the solvent extract with, for example, brine and water, drying it and evaporating off the solvent to obtain the halobenzonorbornadiene (V), which may be further purified by crystallisation from a solvent such as hexane. This reaction is described in WO 2007/068417.

Reaction step b):

Reactions b) can be performed using the methodology described in WO 2007/068417 for the corresponding nitro/amine substituted norbornenes. The extent of hydrogenation may also be controlled e.g. by using Wilkinson's catalyst ($RhCl(PPh_3)_3$). The compound of formula VI may be produced during the course of reaction a or b as described on page 30 of PCT/EP2009/067283. The compounds may be isolated according to known procedures, e.g. HPLC.

Reaction step c):

The compounds of the formula VII may be obtained using standard ozonolysis conditions (in dichloromethane at −70° C.) from 9-alkylidene-benzonorbornenes of the formula VI followed by a reductive work up involving reducing agents such as triphenylphosphane (J. J. Pappas et al, *J. Org. Chem.* 33, 787 (1968), dimethyl sulphide (J. J. Pappas et al, *Tetrahedron Letters*, 7, 4273 (1966), trimethyl phosphite (W. S. Knowles et al, *J. Org. Chem.* 25, 1031 (1960), or zinc/acetic acid (R. Muneyuki and H. Tanida, *J. Org. Chem.* 31, 1988 (1966). Suitable solvents are, for example, dichloromethane, chloroform and methanol.

Reaction step d):

The compounds of formula VIII are obtained by the Wittig olefination of the compounds of formula VII with in situ generated dihalomethylidene phosphoranes $RP=C(Cl)Cl$, where R is triphenyl, tri $C_{1-4}$ alkyl or tridimethylamine, according to or by analogy with the procedures described by H-D. Martin et al, *Chem. Ber.* 118, 2514 (1985), S. Hayashi et al, *Chem. Lett.* 1979, 983, or M. Suda, *Tetrahedron Letters*, 22, 1421 (1981).

Suitable solvents are for example acetonitrile or $CH_2Cl_2$, preferred is acetonitrile. The temperature can vary between ambient temperature and 60° C., preferred is a range of 50-60° C., in particular 60° C. A preferred phosphan is triphenylphosphane which can be used in an amount of 2.2-8 eq., preferred 2.2 eq. The carbon tetrachloride can be used in an amount of 1.5-5 eq, preferred 1.5 eq. The ratio $CCl_4:PPh_3$ is 1:2 up to 1:1.7. The reaction can also be performed with chloroform instead of carbon tetrachloride. Carbon tetrachloride is preferred.

The compound of formula VIII is novel, is especially developed for the process according to the invention and therefore constitutes a further object of the invention.

Reaction step e1):

From the two process variants step e1) to step f) and step e2), the variant step e1) to f) is preferred. The catalyst which comprises palladium and at least one ligand used in the process will generally be formed from a palladium precursor and at least one suitable ligand. Where the process is carried out in a solvent, the complex will normally be soluble in the solvent. In the context of this process palladium complexes expressly include those consisting of cyclic organic palladium compounds ("palladacycles") and secondary phosphane ligands.

The palladium complex may be used as a robust, preformed species or may be formed in situ. Typically it is made by reacting a palladium precursor with at least one suitable ligand. In the case of incomplete transformations, residual amounts of the palladium precursor or ligand may be present undissolved in the reaction mixture.

Useful palladium precursors may be chosen from palladium acetate, palladium chloride, palladium chloride solution, palladium$_2$-(dibenzylidene acetone)$_3$ or palladium-(dibenzylidene acetone)$_2$, palladium-tetrakis (triphenylphosphane), palladium/carbon, palladium dichloro-bis(benzonitrile), palladium-(tris-tert-butylphosphane)$_2$ or a mixture of palladium$_2$-(dibenzylidene acetone)$_3$ and palladium-(tris-t-butylphosphane)$_2$.

Useful ligands are, for example, tertiary phosphane ligands, N-heterocyclic carbene ligands and phosphanic acid ligands. Tertiary phosphane ligands are generally of two types: monodentate and bidentate ligands. A monodentate ligand may occupy one palladium coordination site while a bidentate ligand occupies two coordination sites and hence is able to chelate the palladium species.

The following are examples of tertiary phosphane, N-heterocyclic carbene and phosphanic acid ligands and a palladacycle with a secondary phosphane ligand.

(A) Monodentate phosphane ligands:

Tri-tert-butylphosphane, tri-tert-butylphosphonium tetrafluoroborate ("P(tBu)$_3$HBF$_4$"), tris-ortho-tolylphosphane ("P(oTol)$_3$"), tris-cyclohexylphosphane ("P(Cy)$_3$"), 2-di-tert-butyl-phosphano-1,1'-bisphenyl ("P(tBu)$_2$BiPh"), 2-dicyclohexyl-phosphano-1,1'-bisphenyl ("P(Cy)$_2$BiPh"), 2-dicyclohexylphosphano-2',4',6'-tri-isopropyl-1,1'-bisphenyl ("x-Phos"), and tert-butyl-di-1-adamantyl-phosphane ("P(tBu)(Adam)$_2$").

More information about monodentate phosphane ligands can be found in US-2004-0171833.

(B) Bidentate tertiary phosphane ligands:

(B1) Biphosphane ligands:

(B1.1) Ferrocenyl-Biphosphane ligands ("Josiphos" ligands):

1,1'-bis(diphenylphosphano)ferrocene (dppf), 1,1'-bis(di-tert-butylphosphano)-ferrocene, (R)-(−)-1-[(S)-2-(bis(4-trifluoromethylphenyl)phosphano)ferrocenyl]ethyl-di-tert-butyl-phosphane, (R)-(−)-1-[(S)-2-(di(3,5-bis-trifluoromethylphenyl)phosphano)ferrocenyl]ethyl-dicyclohexylphosphane, (R)-(−)-1-[(S)-2-(di(3,5-bis-trifluoromethylphenyl)phosphano)-ferrocenyl]ethyldi(3,5-dimethylphenyl)phosphane, (R)-(−)-1-[(S)-2-(dicyclohexylphosphano)-ferrocenyl]ethyldi-tert-butylphosphane, (R)-(−)-1-[(S)-2-(dicyclohexylphosphano)ferrocenyl]-ethyldicyclohexylphosphane, (S)-(+)-1-[(R)-2-(dicyclohexylphosphano)ferrocenyl]ethyl-dicyclohexylphosphane, (S)-(+)-1-[(R)-2-(dicyclohexylphosphano)ferrocenyl]ethyldiphenylphosphane, (R)-(−)-1-[(S)-2-(bis(3,5-dimethyl-4-methoxyphenyl)phosphano)ferrocenyl]-ethyldicyclohexylphosphane, (S)-(+)-1-[(R)-2-(difurylphosphano)ferrocenyl]ethyldi-3,5-xylyl-phosphane, (R)-(−)-1-[(S)-2-(diphenylphosphano)ferrocenyl]ethyldi-tert-butylphosphane, (S)-(+)-1-[(R)-2-(diphenylphosphano)ferrocenyl]ethyldi-tert-butylphosphane, (R)-(−)-1-[(S)-2-(diphenylphosphano)ferrocenyl]ethyldicyclohexylphosphane, (R)-(+)-1-[(R)-2-(diphenylphosphano)ferrocenyl]ethyldicyclohexylphosphane, (S)-(+)-1-[(R)-2-(diphenylphosphano)-ferrocenyl]ethyldicyclohexylphosphane, (R)-(−)-1-[(S)-2-(dicyclohexylphosphano)ferrocenyl]-ethyldiphenylphosphane, (R)-(−)-1-[(S)-2-(diphenyl)phosphano)ferrocenyl]ethyldi(3,5-dimethylphenyl)phosphane, (R)-(−)-1-[(S)-2-(di-tert-butyl-phosphano)ferrocenyl]ethyl-di-o-tolylphosphane

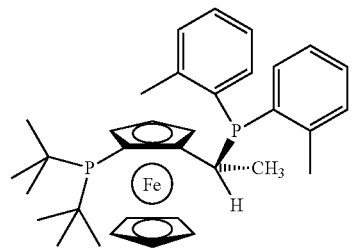

(R)-(−)-1-[(S)-2-(bis(3,5-dimethyl-4-methoxyphenyl)phosphano)ferrocenyl]-ethyl-di-tert-butylphosphane

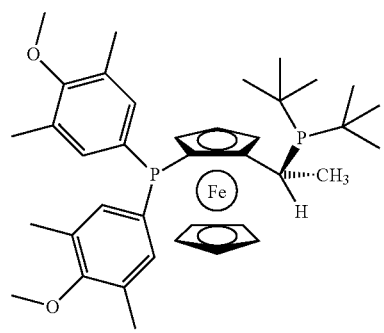

(R)-(−)-1-[(S)-2-(diethylphosphano)ferrocenyl]-ethyl-di-tert-butylphosphane

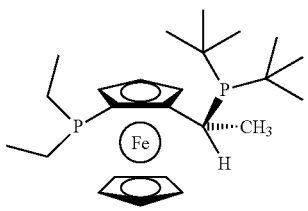

(R)-(−)-1-[(S)-2-(P-methyl-P-isopropyl-phosphano)ferrocenyl]ethyldicyclohexylphosphane

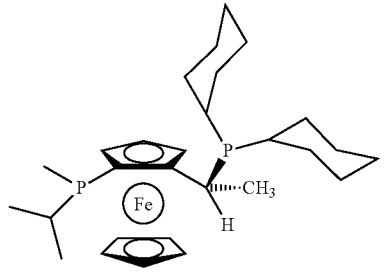

(R)-(−)-1-[(S)-2-(P-methyl-P-phenyl-phosphano)ferrocenyl]ethyl-di-tert-butylphosphane

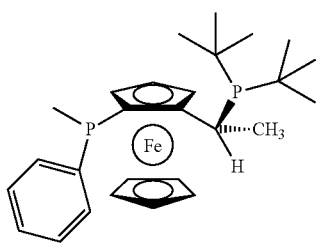

and racemic mixtures thereof, especially racemic mixtures of 1-[2-(di-tert-butylphosphano)-ferrocenyl]ethyl-di-o-tolylphosphane, 1-[2-(dicyclohexylphosphano)ferrocenyl]ethyldi-tert-butylphosphane and 1-[2-(diphenylphosphano)ferrocenyl]ethyldicyclohexylphosphane.

(B1.2) Binaphthyl-bisphosphane ligands:

2,2'bis(diphenylphosphano)-1,1'-binaphthyl ("BINAP"), R-(+)-2,2'-bis(di-p-tolylphosphano)-1,1'-binaphthyl ("Tol-BINAP"), racemic 2,2'-bis(di-p-tolylphosphano)-1,1'-binaphthyl ("racemic Tol-BINAP").

(B1.3) 9,9-Dimethyl-4,5-bis(diphenyl-phosphano)-xanthene ("Xantphos").

(B2) Aminophosphane2 ligands:

(B2.1) Biphenyl ligands:

2-dicyclohexylphosphano-(N,N-dimethylamino)-1,1'-biphenyl ("PCy$_2$NMe$_2$BiPh")

2-di-tert-butylphosphano-(N,N-dimethylamino)-1,1'-biphenyl ("P(tBu)$_2$NMe$_2$BiPh").

(C) N-Heterocyclic carbene ligands:

1,3-bis-(2,6-diisopropylphenyl)-imidazolium chloride ("I—Pr"), 1,2-bis(1-adamantyl)-imidazolium chloride ("I-Ad") and 1,3-bis-(2,6-methylphenyl)-imidazolium chloride ("I-Me").

(D) Phosphanic acid ligands:

di-tert-butyl-phosphanoxide.

(E) Palladacycles containing a secondary phosphane ligand:

the complex of the formula (A-1)

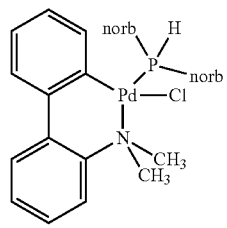

(A-1)

where "norb" is norbornyl, and the complex of the formula (A-2)

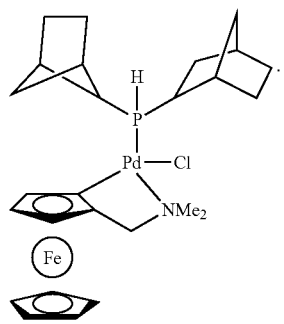

(A-2)

The palladium complex (A-1) is described in *Synlett.*, 2549-2552 (2004) under the code name "SK-CC01-A". The complex (A-2) is described in *Synlett.* (ibid) under the code name "SK-CC02-A".

Further examples of palladium complexes containing phosphanic acid ligands are described in *J. Org. Chem.* 66, 8677-8681 under the code names "POPd", "POPd2" and "POPD1".

Further examples of palladium complexes containing N-heterocyclic carbene ligands are naphthoquinone-1,3-bis(2,6-diisopropylphenyl)imidazole-2-ylidene-palladium (["Pd—NQ-IPr]$_2$"), divinyl-tetramethylsiloxane-1,3-bis(2,6-diisopropylphenyl)imidazole-2-ylidene-palladium ("Pd—VTS—IPr"), 1,3-bis(2,6-diisopropylphenyl)imidazole-2-ylidene-palladium dichloride ("Pd—Cl—IPr"), 1,3-bis(2,6-diisopropylphenyl)imidazole-2-ylidene-palladium diacetate ("Pd—OAc—IPr"), allyl-1,3-bis(2,6-diisopropylphenyl)imidazole-2-ylidene-palladium chloride ("Pd—Al—Cl—IPr") and a compound of the formula (A-3):

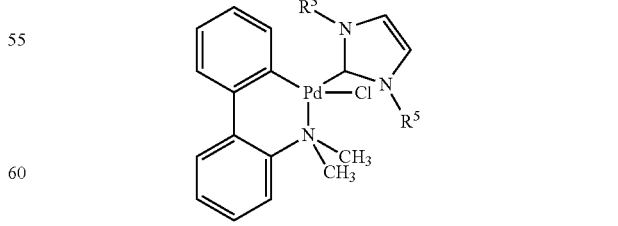

(A-3)

where R$^5$ is 2,6-diisopropylphenyl or 2,4,6-trimethylphenyl. More information about [Pd—NQ-IPr]$_2$, Pd—VTS—IPr, Pd—Cl—IPr, Pd—OAc—IPr and Pd—Al—Cl—IPr can be found in *Organic Letters*, 4, 2229-2231 (2002) and *Syn-*

*lett.*, 275-278, (2005). More information about the compound of formula (A-3) can be found in *Organic Letters*, 5, 1479-1482 (2003).

A single palladium complex or a mixture of different palladium complexes may be used in the process for preparing the compound of the general formula (XI).

Palladium precursors that are particularly useful for the formation of the palladium complexes are those selected from palladium acetate, palladium$_2$-(dibenzylidene acetone)$_3$, palladium-(dibenzylidene acetone)$_2$, palladium chloride solution or a mixture of palladium$_2$-(dibenzylidene acetone)$_3$ and palladium-(tris-tert.-butylphosphane)$_2$. Palladium acetate is especially useful, as is palladium chloride.

At least one ligand is used for the formation of the palladium complex. Normally the palladium complex will have at least one ligand chosen from a monodentate tertiary phosphane ligand, a bidentate teritary phosphane ligand and a N-heterocyclic carbene ligand, and typically at least one ligand chosen from a ferrocenyl-biphosphane ligand, a binaphthyl-bisphosphane ligand and an aminophosphane ligand.

Particularly suitable are palladium complexes that contain at least one ligand selected from tri-tert-butylphospine, P(tBu)$_3$HBF$_4$, P(oTol)$_3$, P(Cy)$_3$, P(tBu)$_2$BiPh, P(Cy)$_2$BiPh, x-Phos, P(tBu)(Adam)$_2$, (R)-(−)-1-[(S)-2-(dicyclohexylphosphano)ferrocenyl]ethyldi-tert-butyl-phosphane, racemic 1-[2-(dicyclohexylphosphano)ferrocenyl]ethyldi-tert-butylphosphane, (R)-(−)-1-[(S)-2-(di-tert-butyl-phosphano) ferrocenyl]ethyldi-o-tolylphosphane, racemic 1-[2-(di-tert-butyl-phosphano)ferrocenyl]ethyldi-o-tolylphosphane, dppf, 1,1'-bis(di-tert-butyl-phosphano)-ferrocene, (R)-(−)-1-[(S)-2-(diphenylphosphano)ferrocenyl]ethyldicyclohexylphosphane, racemic 1-[2-(diphenylphosphano)ferrocenyl]ethyldicyclohexylphosphane, (R)-(−)-1-[(S)-2-(diphenylphosphano)ferrocenyl]ethyldi-tert-butylphosphane, BINAP, Tol-BINAP, racemic Tol-BINAP, Xantphos, PCy$_2$NMe$_2$BiPh, P(tBu)$_2$NMe$_2$BiPh, I—Pr, I-Ad and I-Me, and a palladium complex of formula (A-3), where R$^5$ is 2,6-diisopropylphenyl or 2,4,6-trimethyl-phenyl.

Preferred are palladium complexes with at least one ligand selected from tri-tert-butylphospine, P(tBu)$_3$HBF$_4$, P(tBu)$_2$BiPh, P(Cy)$_2$BiPh, x-Phos, (R)-(−)-1-[(S)-2-(dicyclohexylphosphano)ferrocenyl]ethyldi-tert-butylphosphane, racemic 1-[2-(dicyclohexylphosphano)ferrocenyl]ethyldi-tert-butylphosphane, (R)-(−)-1-[(S)-2-(di-tert-butyl-phosphano)ferrocenyl]ethyldi-o-tolylphosphane, racemic 1-[2-(di-tert-butyl-phosphano)ferrocenyl]ethyldi-o-tolylphosphane, dppf, PCy$_2$NMe$_2$BiPh and I—Pr.

Of special interest are palladium complexes that contain at least one ligand selected from the following groups:

(i) tri-tert-butylphospine, P(tBu)$_3$HBF$_4$, P(tBu)$_2$BiPh, P(Cy)$_2$BiPh, x-Phos, PCy$_2$NMe$_2$BiPh and I—Pr;

(ii) tri-tert-butylphospine, P(tBu)$_3$HBF$_4$, PCy$_2$NMe$_2$BiPh and I—Pr;

(iii) tri-tert-butylphospine and P(tBu)$_3$HBF$_4$; and (iv) (R)-(−)-1-[(S)-2-(dicyclohexylphosphano)ferrocenyl] ethyldi-tert-butylphosphane and racemic 1-[2-(dicyclohexylphosphano)ferrocenyl]ethyldi-tert-butylphosphane.

Preferred are palladium complexes that contain as a ligand PCy$_2$NMe$_2$BiPh, I—Pr, (R)-(−)-1-[(S)-2-(dicyclohexylphosphano)ferrocenyl]ethyldi-tert-butylphosphane or racemic 1-[2-(dicyclohexylphosphano)ferrocenyl]ethyldi-tert-butylphosphane.

A preferred complex is one where the precursor is palladium chloride and the ligand is (R)-(−)-1-[(S)-2-(dicyclohexylphosphano)ferrocenyl]ethyldi-tert-butylphosphane.

The palladium complex is used in the preparation of the compound of formula (II) in a catalytic amount, normally in a molar ratio of from 1:10 to 1:10000 in respect to the compound of formula (IV), typically in a ratio of 1:100 to 1:1000, for example, 1:500 to 1:700 or about 1:600. The complex may be pre-formed or formed in situ by mixing together the precursor and ligand, which will generally be used in equimolar amounts, or thereabouts.

An especially preferred palladium catalyst for reaction step f) is Pd(OAc)$_2$ (preferred loading is 3-5 mol %, in particular 4 mol %), a ligand selected from the Josiphos, DavePhos (e.g. 2-dicyclohexylphosphano-2'-(N,N-dimethylamino)biphenyl) or Xantphos 4,5-Bis(diphenylphosphano)-9,9-dimethylxanthene) types, preferred is the Josiphos type, in particular Josiphos SL-J009-1 which is (2R)-1-[(1R)-1-[bis(1,1-dimethylethyl)phosphano]ethyl]-2-(dicyclohexylphosphano) ferrocene (preferred amount is 3-5 mol %, in particular 4.4 mol %.

NH$_3$ is advantageously added under a pressure of 0.9 to 1.1 MPa, preferably 1 to 1.05 MPa. The reaction step is preferably performed at temperatures from 80 to 150° C., preferably 100 to 120° C. at pressures from 1.4 to 2.6 MPa, preferably 1.5 to 2.2 MPa, in particular 2.2 MPa. Preferred solvents are ethers like dimethylether.

Reaction step f):

The compound of formula X is known and is disclosed, for example, in U.S. Pat. No. 5,093,347.

Preferred bases for reaction step f) are amines like triethylamine, or sodium or potassium carbonate or bicarbonate, or NaOH, preferably triethylamine or NaOH.

Preferred solvents are xylene, toluene or chlorobenzene. The reaction is preferably performed at temperatures from −10 to 90° C., preferably from 70 to 80° C.

Reaction step e2):

The compound of formula Xa is for example described in PCT/EP2009/067286.

The reaction step e2) can be performed at temperatures from 100 to 180° C., preferably at 130° C. Heating is possible in a sealed vial, open flask, under reflux or under microwave irradiation, preferably in a sealed vial.

As solvents can be used amides (DMF, NMP), alcohols (cyclohexanol), ethers (diglyme, dioxane), sulfoxides (DMSO), hydrocarbons (mesitylene, toluene), nitriles (butyronitrile) and mixtures thereof (toluene/methanol, toluene/cyclohexanol, dioxane/methanol, dioxane/water), preferably toluene and dioxane.

As copper sources can be used Cu(0), Cu(I) or Cu(II) salts. Examples are Cu(0) powder, Cu(I) iodide, Cu(I) thiophenecarboxylate, Cu(II) phthalocyanine, Cu(II) acetate, Cu(II) oxide, Cu(II) chloride, Cu(II) bromide, Cu(II) sulfate pentahydrate and mixtures thereof, preferably Cu(II) oxide and Cu(II) chloride.

The copper catalyst can be used in amounts between 2 and 330 mol-%, preferably 8-12 mol-%, in particular 10 mol-%. If Cu(0) is used, the amount is preferably >100 mol %.

Ligands are generally required for effective catalysis. Examples are N,N'-dimethylethylenediamine, 1,2-bisdimethylaminocyclohexane, 1,2-diaminocyclohexane, 1,2-phenylenediamine, 4-dimethylaminopyridine, 1,2-bis(3-aminopropylamino)ethane, triethylenetetramine, diethylenetriamine, Tris(2-aminoethyl)amine. Preferably, N,N'-dimethylethylenediamine is used. Carbonates can be used as the base, for example cesium carbonate and preferably potassium carbonate. The conversion is generally completed after 5-24 hours.

PREPARATORY EXAMPLES

Step a): Preparation of 5-bromo-9-isopropylidene-1,4-dihydro-1,4-methano-naphthalene of Formula Va

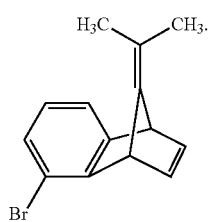

(Va)

To a stirred solution of 1,2,3-tribromo-benzene (4.34 g, 13.8 mmol) and 6,6-dimethylfulvene (2.38 g, assay 92.6%, 20.7 mmol) in dry toluene (60 ml) under a nitrogen atmosphere, 5.5 ml of a 2.5M toluene solution of n-butyllithium (14.5 mmol) were added dropwise at −5 to 0° C. within 10 minutes. After a further 10 minutes at 0° C. and 2 hours at ambient temperature, the reaction mixture was poured onto a saturated aqueous solution of ammonium chloride, extracted with ethyl acetate, washed with brine and water, dried over sodium sulphate and evaporated. Purification of the crude material on silca gel in hexane afforded 2.38 g of the desired product as a yellow oil (assay 84% by g.l.c., 55% yield). This reaction is also disclosed in WO 2007/068417.

Preparation of 5-chloro-9-isopropylidene-1,4-dihydro-1,4-methano-naphthalene of Formula Vb

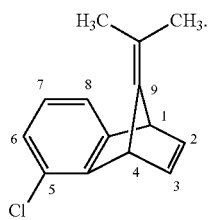

(Vb)

A solution of 2-bromo-1,3-dichlorobenzene (22.59 g, 0.1 mol) in dry toluene (100 ml) under a nitrogen atmosphere was reacted at −8 to −15° C. with 2M isopropylmagnesium chloride in tetrahydrofuran (50 ml, 0.1 mol) for 1 hour. Subsequent addition of 6,6-dimethylfulvene (13.03 g, assay 97.8%, 0.12 mol) at 0° C. was followed by heating to reflux temperature for 10 hours. Aqueous work up with saturated aqueous ammonium chloride and ethyl acetate extraction followed by washings with brine and water and drying over sodium sulphate gave the crude material which was purified by chromatography on silica gel in hexane to give the desired product (19.03 g, assay 95.2% by g.l.c., 83.6% yield) as a yellow solid. This reaction is also disclosed in WO 2007/068417.

Step b): Preparation of 5-chloro-9-isopropylidene-1,2,3,4-tetrahydro-1,4-methano-naphthalene of Formula VIa

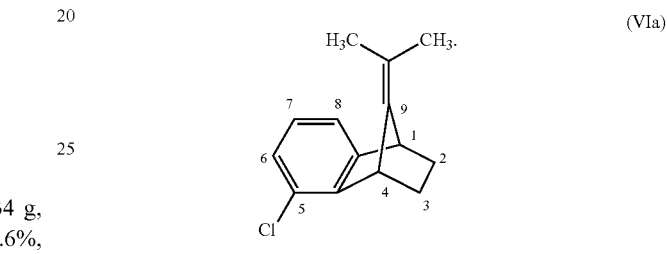

(VIa)

170 g of 5-Chloro-9-isopropylidene-1,4-dihydro-1,4-methano-naphthalene (0.785 mol), 0.5 g of Pd 10% (0.2 mmol) and 1 liter THF were charged in an hydrogenation reactor. 19 liter Hydrogen was feed at ambient temperature; the reaction was carried out at 0.05 MPa pressure. After complete conversion, the reaction mixture was filtered off over hyflo and product solution was evaporated to give 167 g product (Purity: 92%; Yield: 90%). The product was crystallized with MeOH, filtered off and dried. Purity: 97.54%

NMR (CDCl$_3$): 7.0-7.1 ppm (m, 3H, aromatic), 4.05 ppm (m, 1H, CH), 3.85 ppm (m, 1H, CH), 1.9-2 ppm (m, 2H, CH$_2$), 1.7 (s, 3H, CH$_3$), 1.65 (s, 3H, CH$_3$), 1.2-1.3 (m, 2H, CH$_2$).

Step c): Preparation of 5-chloro-1,2,3,4-tetrahydro-1,4-methano-naphthalen-9-one of Formula VIIa

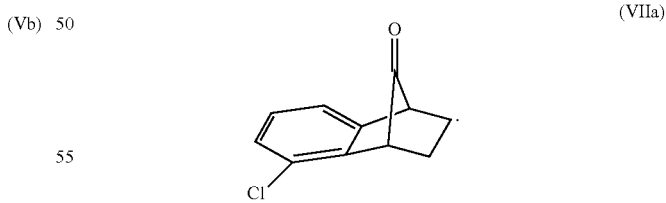

(VIIa)

In a 20 liter reactor, 600 g of 5-chloro-9-isopropylidene-1,2,3,4-tetrahydro-1,4-methano-naphthalene (27.43 mol) were charged in a mixture of 13 l CH$_2$Cl$_2$ and 0.5 l of MeOH. The reaction mixture was cooled down at −40° C. and an ozone stream (55 kg/h) was feed until change of color. After elimination of the ozone residue, PPh$_3$ (23.83 mol) was added and reaction mixture was heated to ambient temperature. The purification was done via chromatography. 421 g white solid product was isolated with a purity >98%.

NMR (CDCl$_3$): 7.1-7.3 ppm (m, 3H, aromatic), 3.6 ppm (d, 1H, CH), 3.4 ppm (d, 1H, CH), 2.1-2.3 ppm (m, 2H, CH$_2$), 1.3-1.5 ppm (m, 2H, CH$_2$).

Step d): Preparation of 5-chloro-9-dichloromethylene-1,2,3,4-tetrahydro-1,4-methano-naphthalene of Formula VIIIa

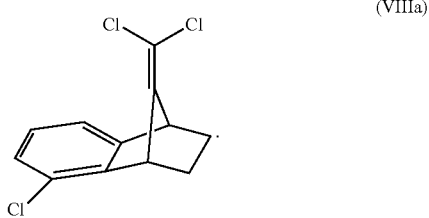 [SMILES: ClC(Cl)=C1C2CC[C@H]1c1c(Cl)cccc12 ; "."]

(VIIIa)

To a solution of 50 g of 5-chloro-1,2,3,4-tetrahydro-1,4-methano-naphthalen-9-one and 520 ml acetonitrile, 157 g (2.2 eq) PPh$_3$ was added in portion at ambient temperature. Then 60 g CCl$_4$ (1.5 eq) were feed over 40 min. The reaction mixture was heated to 60° C. and stirred until complete conversion. The reaction mixture was distilled off to give 259 g crude oil. 500 g ice water and 500 ml CH$_2$Cl$_2$ were added. After phase separation, the aqueous phase was washed with CH$_2$Cl$_2$. The combined organic phases were washed with brine and the organic phases distilled off.

To purify the crude oil, 400 ml acetone was added and the oil was dissolved at 50° C. By adding 500 ml hexane, product was precipitated. The product was filtered off and washed with 150 ml hexane. The mother liquor was evaporated and recrystallised as described previously; this operation was repeated twice. In total, 66.1 g brown oil was obtained; this latter was purified over silica (AcOEt/cyclohexane: 1/9) to give 62.8 g of the compound of formula VIIa. Yield: 93.2%.

$^1$H-NMR (400 MHz, CDCl$_3$): δ=7.13-7.03 (m, 3H, Ar—H); 4.18-4.17 (m, 1H); 3.97-3.96 (m, 1H); 2.15-2.07 (m, 2H); 1.45-1.32 (m, 2H).

Step e1): Preparation of 9-dichloromethylene-1,2,3,4-tetrahydro-1,4-methano-naphthalen-5-ylamine of Formula IX Starting from 5-bromo-9-dichloromethylene-1,2,3,4-tetrahydro-1,4-methano-naphthalene

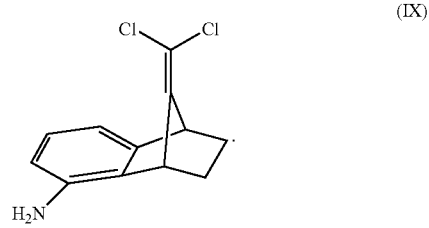 [SMILES: Nc1cccc2c1[C@@H]1CCC2C1=C(Cl)Cl ; "."]

(IX)

Catalyst preparation: 8.98 mg of palladium acetate (0.040 mmol) and 22 mg of Josiphos Ligand (Josiphos SL-J009-1, (2R)-1-[(1R)-1-[bis(1,1-dimethylethyl)phosphano]ethyl]-2-(dicyclohexylphosphano)ferrocene (Solvias AG), 0.040 mmol) were placed in a 5 ml Schlenk tube and inertized with argon/vacuum. 2.5 ml dimethylether was added and the catalyst was left stirring for 15 min.

Starting-material solution: 608 mg of 5-bromo-9-dichloromethylene-1,2,3,4-tetrahydro-1,4-methano-naphthalene (2 mmol) was placed in a 5 ml Schlenk tube and inertized with argon/vacuum. 2.5 ml degassed dimethylether was then added to the starting material.

Reaction: 384 mg of NaOtBu (4 mmol) was placed in the stainless steel 50 ml autoclave. The autoclave was screwed on and set under argon. Under a constant flow of argon, the starting material solution was transferred into the autoclave, followed by the catalyst solution. NH$_3$ was added until pressure reached 1.05 MPa. The autoclave was heated to 105° C., pressure increased to 1.6 MPa. After 32 hour reaction, the reaction was stopped. 79% product was identified by HPLC.

The compound of formula IX can be prepared analogously with 5-chloro-9-dichloromethylene-1,2,3,4-tetrahydro-1,4-methano-naphthalene as starting material.

Step f): Preparation of 3-difluoromethyl-1-methyl-1H-pyrazole-4-carboxylic acid (9-dichloromethylene-1,2,3,4-tetrahydro-1,4-methano-naphthalen-5-yl)-amide of Formula I

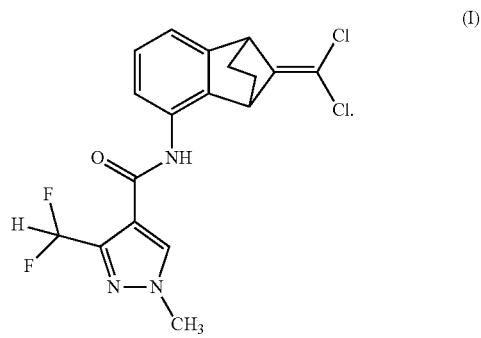 [SMILES: Cn1cc(C(=O)Nc2cccc3c2C2CCC3C2=C(Cl)Cl)c(C(F)F)n1]

(I)

9-Dichloromethylene-1,2,3,4-tetrahydro-1,4-methano-naphthalen-5-ylamine (166 g, 35% xylene solution, 0.25 mol), triethylamine (28 g, 0.275 mol) and xylene (13 g) were charged in a reactor and the mixture was heated to 80° C. 3-Difluoromethyl-1-methyl-1H-pyrazole-4-carbonyl chloride (182 g, 26% xylene solution, 0.25 mol) was added over 2 hours. After conversion, the product was extracted, concentrated and crystallized in a mixture of xylene/methycyclohexane. 83 g of pure product were isolated. (Purity: 97%, Yield: 82%)

$^1$H-NMR (400 MHz, CDCl$_3$): δ=8.12 (bs, 1H, NH); 8.05 (s, 1H, Pyr-H); 7.83-7.80 (d, 1H, Ar—H); 7.19-7.15 (t, 1H, Ar—H); 7.04 (d, 1H, Ar—H); 7.02-6.76 (t, 1H, CHF$_2$); 4.1 (s, 1H, CH); 3.95-4.0 (bs, 4H, CH & CH$_3$); 2.18-2.08 (m, 2H, CH$_2$); 1.55-1.3 (2m, 2H, CH$_2$).

Step e2): Preparation of 3-difluoromethyl-1-methyl-1H-pyrazole-4-carboxylic acid (9-dichloromethylene-1,2,3,4-tetrahydro-1,4-methano-naphthalen-5-yl)-amide of Formula I A 20 ml screw-cap vial was filled with the following solids: CuO (0.05 mmol, 4.0 mg), anhydrous CuCl$_2$ (0.05 mmol, 6.7 mg), K$_2$CO$_3$ (2.0 mmol, 277 mg), 3-difluoromethyl-1-methyl-1H-pyrazole-4-carboxylic acid amide (1.1 mmol, 193 mg) and 5-bromo-9-dichloromethylene-1,2,3,4-tetrahydro-1,4-methano-naphthalene (1.0 mmol, 304 mg). A magnetic stir bar was added, and the open vial was gently flushed with N$_2$. Dioxane (2 mL) was added, followed by N,N'-dimethylethylenediamine (0.45 mmol, 48 μl). The vial was sealed and placed into a preheated screening block at 130° C. Conversion was complete after 24 hours. The yield (HPLC-analysis) of the compound of formula I was 70%.

The reaction can be performed analogously using 5,9,9-trichloromethylene-1,2,3,4-tetrahydro-1,4-methano-naphthalene as starting material.

What is claimed is:

1. A process for the preparation of the compound of formula I

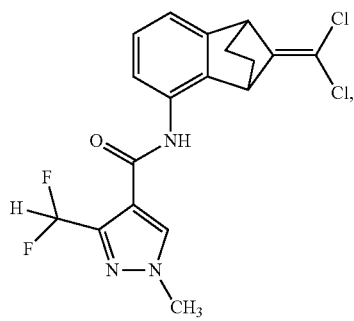

(I)

which process comprises a) reacting a compound of formula II

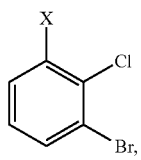

(II)

wherein X is chloro or bromo, with an organometallic species in an inert atmosphere to a halobenzyne of formula III

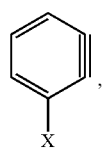

(III)

wherein X is chloro or bromo; reacting the halobenzyne of formula III so formed with a fulvene of formula IV

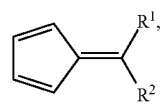

(IV)

wherein $R^1$ and $R^2$ are independently hydrogen or $C_1$-$C_6$alkyl; to a compound of formula V

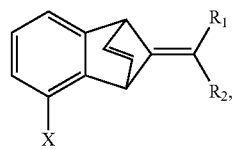

(V)

wherein $R^1$ and $R^2$ are independently hydrogen or $C_1$-$C_6$alkyl and X is chloro or bromo;

b) hydrogenating the compound of formula V in the presence of a suitable metal catalyst to a compound of formula VI

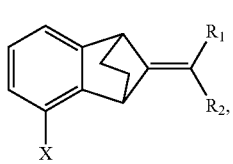

(VI)

wherein $R^1$ and $R^2$ are independently hydrogen or $C_1$-$C_6$alkyl and X is chloro or bromo;

c) ozonising the compound of formula VI to a compound of formula VII

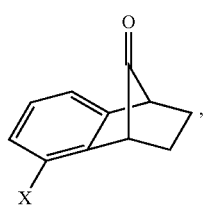

(VII)

wherein X is chloro or bromo;

d) converting the compound of formula VII in the presence of a phosphane and $CCl_4$ or $CHCl_3$ to the compound of formula VIII

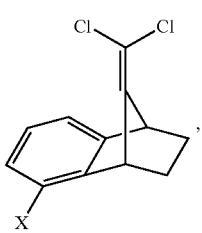

(VIII)

wherein X is chloro or bromo; and either e1) reacting the compound of formula VIII with $NH_3$ in the presence of a catalyst comprising palladium and at least one ligand to the compound of formula IX (IX)

[structure: bicyclic compound with =CCl₂ group and H₂N substituent on aromatic ring]

and f) reacting the compound of formula IX in the presence of a base with the compound of formula X (X)

[structure: pyrazole with C(O)Cl, CHF₂, and N-CH₃ substituents]

to the compound of formula I; or
e2) reacting the compound of formula VIII (VIII)

[structure: bicyclic compound with =CCl₂ group and X substituent on aromatic ring]

wherein X is chloro or bromo; in the presence of a solvent, a base, a copper catalyst and at least one ligand with the compound of formula Xa (Xa)

[structure: pyrazole with C(O)NH₂, CHF₂, and N-CH₃ substituents]

to the compound of formula I.

2. A process according to claim 1, wherein in step a) the organometallic species is selected from C$_{1-6}$ alkyl- or phenyllithium halides and C$_{1-6}$ alkyl- or phenylmagnesium halides.

3. A process according to claim 1, wherein in step d) the compound of formula VII is converted into the compound of formula VIII in the presence of triphenylphosphane and carbontetrachloride.

4. A process according to claim 1, wherein in step e) the ligand is selected from ferrocenyl-biphosphane ligands.

5. A process according to claim 1, which comprises reacting the compound of formula VIII with NH₃ in the presence of a catalyst comprising palladium and at least one ligand to the compound of formula IX (IX)

[structure: bicyclic compound with =CCl₂ group and H₂N substituent on aromatic ring]

and reacting the compound of formula IX in the presence of a base with a compound of formula X (X)

[structure: pyrazole with C(O)Cl, CHF₂, and N-CH₃ substituents]

to the compound of formula I.

6. The compound of formula VIII (VIII)

[structure: bicyclic compound with =CCl₂ group and X substituent on aromatic ring]

wherein X is chloro or bromo.

* * * * *